United States Patent
Fukunaga et al.

[11] Patent Number: 6,003,511
[45] Date of Patent: *Dec. 21, 1999

[54] RESPIRATORY CIRCUIT TERMINAL FOR A UNILIMB RESPIRATORY DEVICE

[75] Inventors: Atsuo F. Fukunaga; Blanca M. Fukunaga, both of Rancho Palos Verdes, Calif.

[73] Assignee: Medlis Corp., Rancho Palos Verdes, Calif.

[*] Notice: This patent is subject to a terminal disclaimer.

[21] Appl. No.: 09/115,766

[22] Filed: Jul. 15, 1998

Related U.S. Application Data

[62] Division of application No. 09/018,540, Feb. 4, 1998, which is a division of application No. 08/751,316, Nov. 18, 1996, Pat. No. 5,778,872.

[51] Int. Cl.$^6$ .................................................. A62B 9/04
[52] U.S. Cl. ............................. 128/202.27; 128/205.29; 128/207.14; 128/911; 128/912; 128/914
[58] Field of Search ................... 128/205.12, 205.27, 128/205.29, 205.17, 202.27, 203.26, 204.18, 204.22, 204.25, 204.26, 206.15, 207.14, 911, 912, 200.14, 200.18, 200.24, 914; 55/DIG. 35; 96/286

[56] References Cited

U.S. PATENT DOCUMENTS

| | | |
|---|---|---|
| 3,556,097 | 1/1971 | Wallace . |
| 3,713,440 | 1/1973 | Nicholes . |
| 3,856,051 | 12/1974 | Bain . |
| 4,007,737 | 2/1977 | Paluch . |
| 4,148,732 | 4/1979 | Burrow et al. . |
| 4,188,946 | 2/1980 | Watson et al. . |
| 4,232,667 | 11/1980 | Chalon et al. . |
| 4,265,235 | 5/1981 | Fukunaga . |
| 4,269,194 | 5/1981 | Rayburn et al. . |
| 4,391,271 | 7/1983 | Blanco . |
| 4,463,755 | 8/1984 | Suzuki . |
| 4,621,634 | 11/1986 | Nowacki et al. . |
| 4,637,384 | 1/1987 | Schroeder . |
| 4,657,532 | 4/1987 | Osterholm . |
| 5,140,983 | 8/1992 | Jinotti . |
| 5,284,160 | 2/1994 | Dryden . |
| 5,404,873 | 4/1995 | Leagre et al. . |
| 5,546,930 | 8/1996 | Wikefeldt . |
| 5,722,391 | 3/1998 | Rosenkoetter et al. ............ 128/200.24 |

FOREIGN PATENT DOCUMENTS

| | | |
|---|---|---|
| 93941 | 8/1923 | Austria . |
| WO/85 277 | 12/1985 | WIPO . |

OTHER PUBLICATIONS

Dorsch, Jerry A., M.D., Dorsch, Susan E., M.D., *Understanding Anesthesia Equipment*, Chapter 7, The Circle Absorption System, pp. 201–202 and 220–221.

Andrews, J. Jeffrey., Inhaled Anesthetic Delivery, Anesthesia, Fourth Edition, pp. 185; and 203–207.

*Primary Examiner*—John G. Weiss
*Assistant Examiner*—Joseph F. Weiss, Jr.
*Attorney, Agent, or Firm*—Bose McKinney & Evans LLP

[57] ABSTRACT

A method for providing assisted ventilation which avoids hypoxia and hypocapnia is disclosed, in which a predetermined dead space in an assisted ventilation system is provided external to the patient. The method may also be used to create normocapnia or moderate hypercapnia without causing hypoxia during assisted ventilation. Preferably, hypoxia can be avoided while inducing and/or maintaining the arterial carbon dioxide tension between about 35 and 95 mmHg. Dead space volumes as small as 10 ml and exceeding 150 ml are utilized in the method. An improved proximal terminal, tubular attachments, and coaxial filter are disclosed, which are safer the less expensive to use than prior art unilimb assisted ventilation systems; the devices of the present invention also reduce medical wastes in comparison to prior art assisted ventilation systems. An interface is provided, which incorporates the proximal terminal and other functional devices, to which tubular respiratory conduits of predetermined and/or adjustable dead space volumes can be connected.

20 Claims, 8 Drawing Sheets

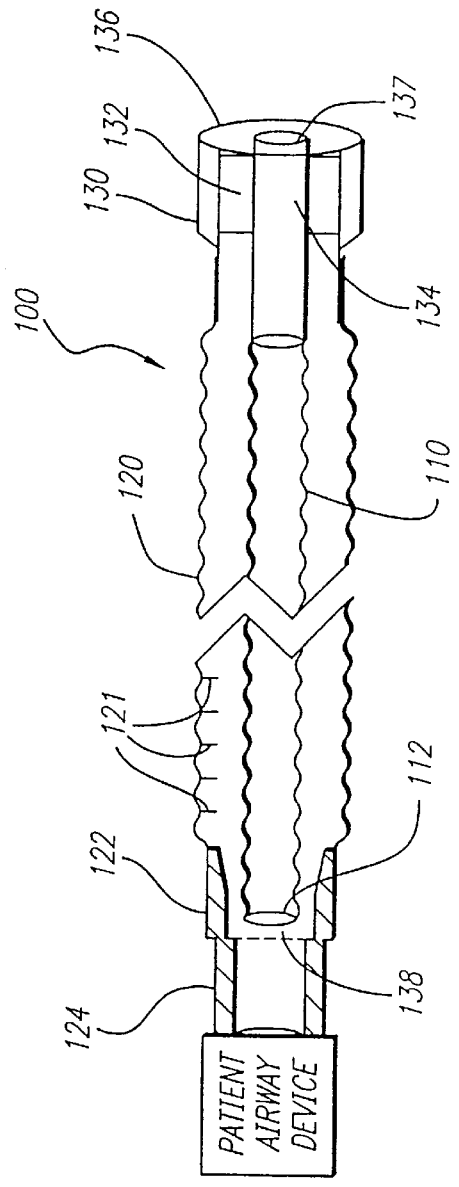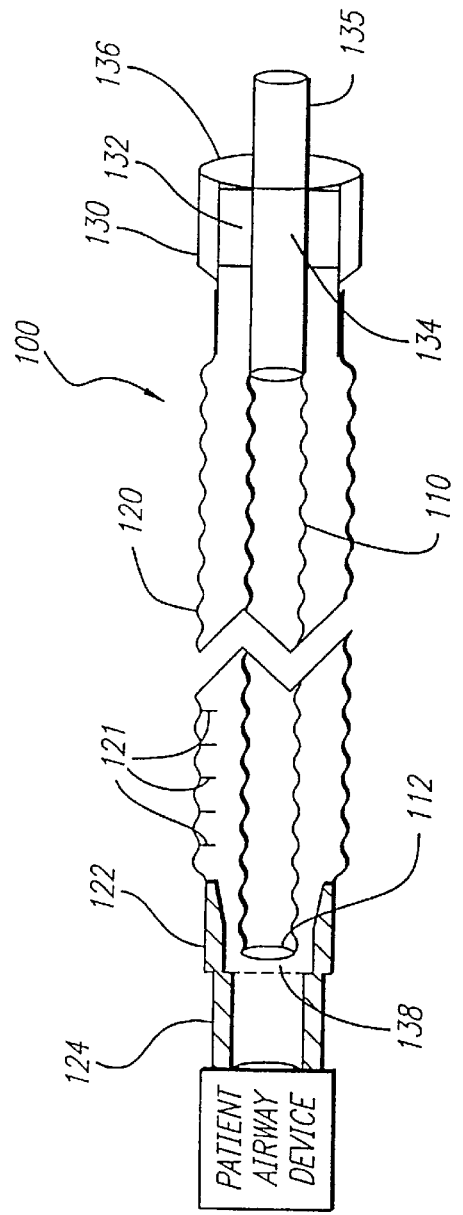

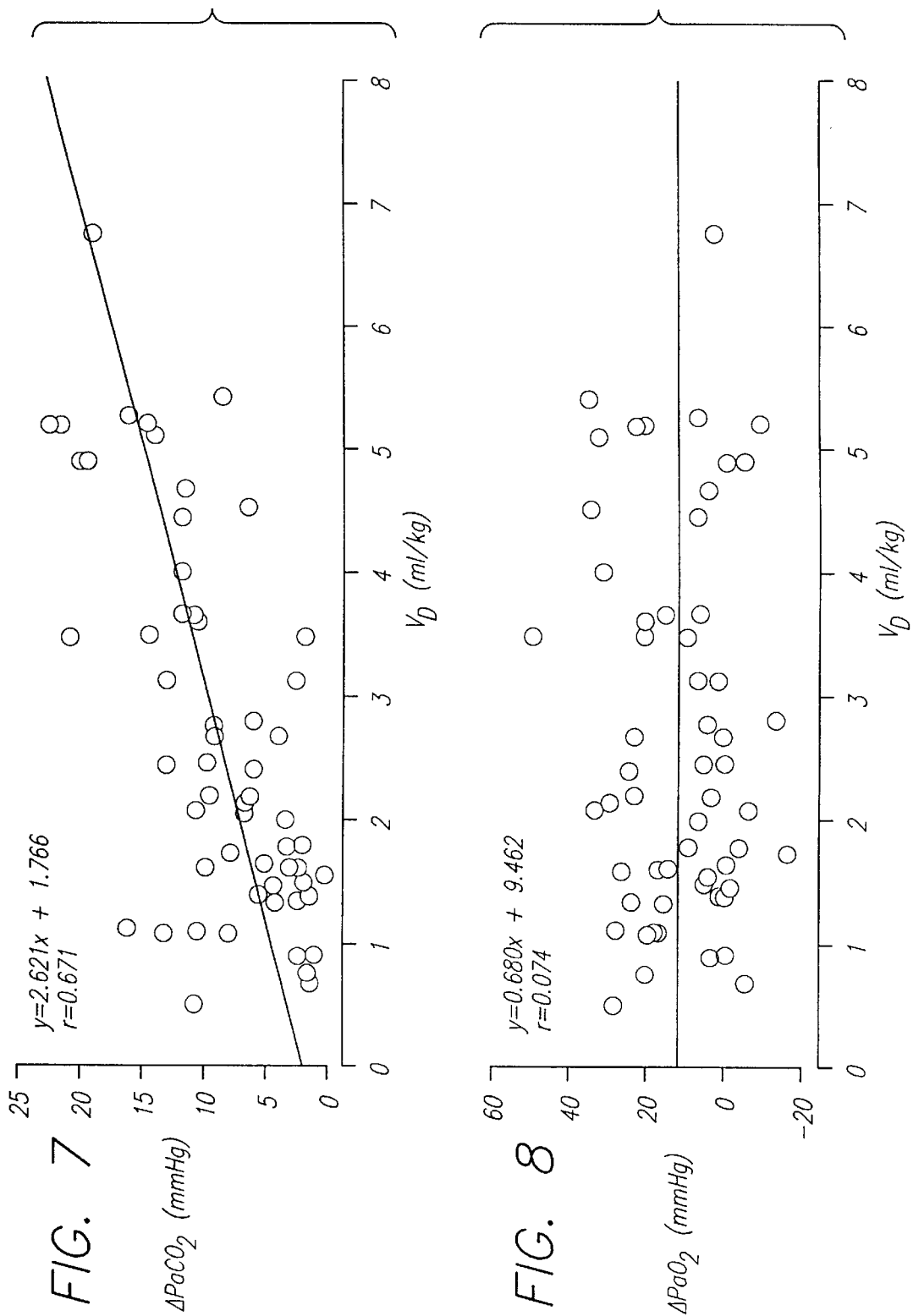

FIG. 10

THE RATE OF INCREASE IN ARTERIAL BLOOD CARBON DIOXIDE TENSION
IN RELATION TO APPARATUS DEAD SPACE

[ $\Delta PCO_2$ (mmHg) VS VD (ml) ]

| WEIGHT (kg) | \multicolumn{16}{c}{DEAD SPACE VOLUME (ml)} |
|---|---|---|---|---|---|---|---|---|---|---|---|---|---|---|---|---|
| | 10 | 20 | 30 | 40 | 50 | 100 | 200 | 300 | 400 | 500 | 600 | 700 | 800 | 900 | 1000 |
| 3 | 11 | 19 | 28 | 37 | 45 | 89 | 176 | 264 | | | | | | | |
| 10 | 4 | 7 | 10 | 12 | 15 | 28 | 54 | 80 | 107 | 133 | 159 | 185 | 211 | 238 | 264 |
| 20 | 3 | 4 | 6 | 7 | 8 | 15 | 28 | 41 | 54 | 67 | 80 | 94 | 107 | 120 | 133 |
| 30 | 3 | 4 | 4 | 5 | 6 | 11 | 19 | 28 | 37 | 45 | 54 | 63 | 72 | 80 | 89 |
| 40 | 2 | 3 | 4 | 4 | 5 | 8 | 15 | 21 | 28 | 35 | 41 | 48 | 54 | 61 | 67 |
| 50 | 2 | 3 | 3 | 4 | 4 | 7 | 12 | 17 | 23 | 28 | 33 | 38 | 44 | 49 | 54 |
| 60 | 2 | 3 | 3 | 3 | 4 | 6 | 11 | 15 | 19 | 24 | 28 | 32 | 37 | 41 | 45 |
| 70 | 2 | 2 | 3 | 3 | 3 | 6 | 9 | 13 | 17 | 20 | 24 | 28 | 32 | 35 | 39 |
| 80 | 2 | 2 | 3 | 3 | 3 | 5 | 8 | 12 | 15 | 18 | 21 | 25 | 28 | 31 | 35 |
| 90 | 2 | 2 | 3 | 3 | 3 | 5 | 8 | 11 | 13 | 16 | 19 | 22 | 25 | 28 | 31 |
| 100 | 2 | 2 | 3 | 3 | 3 | 4 | 7 | 10 | 12 | 15 | 17 | 20 | 23 | 25 | 28 |

$\Delta PCO_2$ (mmHg) = 2.621 × VD (ml/kg) + 1.766 (FROM STUDY II)

RESPIRATORY CIRCUIT TERMINAL FOR A UNILIMB RESPIRATORY DEVICE

This is a division of application Ser. No. 09/018,540, filed Feb. 4, 1998, which is a division of application Ser. No. 08/751,316 filed Nov. 18, 1996, now U.S. Pat. No. 5,778, 872.

FIELD OF THE INVENTION

The present invention relates in one aspect to artificial ventilation methods and systems for administering and exhausting gases to a mammal, including methods and systems for use in anesthesia and administration of oxygen to patients, and more particularly to artificial breathing systems capable of controlling carbon dioxide rebreathing. The present invention relates in another aspect to a unilimb inspiratory and expiratory breathing device for use in a breathing circuit, which has one or more tubular conduits detachable at a common interface, the interface optionally providing for control of gas flow and operable connection to different functional devices.

BACKGROUND OF THE INVENTION

Breathing circuits are utilized to conduct inspiratory gases from a source of same, such as from an anesthetic machine, to a patient, and to conduct expiratory gases away from the patient. The gases are conducted through two or more conduits, and, generally, at least a portion of the expiratory gas is recycled to the patient after removal of carbon dioxide. To facilitate description of the prior art and the present invention, the end of a conduit directed toward a patient shall be referred to as the distal end, and the end of a conduit facing or connected to a source of inspiratory gases shall be referred to as the proximal end. Likewise, fittings and terminals at the distal end of the breathing circuit, e.g., connecting to or directed at the patient airway device (i.e., endotracheal tube, laryngeal mask, or face mask), will be referred to as distal fittings or terminals, and fittings and terminals at the proximal end of the breathing circuit will be referred to as proximal fittings and terminals. For further information on breathing systems, and anesthetic ventilation techniques, see U.S. Pat. No. 3,556,097, U.S. Pat. No. 3,856,051, U.S. Pat. No. 4,007,737, U.S. Pat. No. 4,188,946, U.S. Pat. No. 4,232,667, U.S. Pat. No. 5,284,160, Austrian Patent No. 93,941, Dorsch, J. A., and Dorsch, S. E., Understanding Anesthesia Equipment: Construction, Care and Complications, Williams & Wilkins Co., Baltimore (1974) (particularly chapters 5–7), and Andrews, J. J., "Inhaled Anesthetic Delivery Systems," in Anesthesia, Fourth Edition, Miller, Ronald, M.D., Editor, Churchill Livingstone Inc., New York (1986), (particularly pp. 203–207). The text of all documents referenced herein, including documents referenced within referenced documents, is hereby incorporated as if same were reproduced in full below.

U.S. Pat. No. 4,265,235, to Fukunaga, describes a unilimb device of universal application for use in different types of breathing systems, which provides many advantages over prior systems. The Fukunaga system utilizes a space saving coaxial, or tube-within-a-tube, design to provide inspiratory gases and remove expiratory gases. Generally, the inner tube is connected at its proximal end to a source of inspiratory, fresh gas, while the outer tube proximal end is connected to an exhaust port and/or to a carbon dioxide absorber (the latter at least partially exhausts into the inspiratory gas source when used in a circle system). In addition to reducing the size of the breathing apparatus connected to a patient by reducing the number of tubes near the patient, the Fukunaga system has additional benefits, such as serving as an artificial nose (expired air warms and humidifies inspired air as the opposing two flows are co-axial in the unilimb device). The Fukunaga circuit is also safer than prior co-axial systems, since the distal end of the inner tube is not connected to the outer tube at a distal fitting, so that the outer tube can be axially extended with respect to the inner tube without disconnecting the proximal end of the inner tube from the source of inspiratory gases; this safety feature can also be used to increase the dead space between the distal ends of the inner tube and outer tube, and thereby allow for adjustment of the amount of expiratory air the patient rebreaths. Dead space is defined herein as the part of the breathing circuit external to the patient which, at the end of expiration, is filled with exhaled gases to be inhaled at the next breath (generally the expired air in the dead space is combined with oxygen and/or other gases provided from a source thereof).

An embodiment of the Fukunaga unilimb device is commercially manufactured as the UNIVERSAL F™ by King Systems of Noblesville, Ind., USA. The device includes a proximal terminal comprising a hollow, T-shaped housing with three ports: an inspiratory gas port, an expiratory gas port at a perpendicular angle to the inspiratory gas port, and a third ("patient") port. The proximal terminal is connected to an outer tube and a coaxial inner tube, which carry gases to and from the proximal terminal. The outer tube is flexible and corrugated, and formed of a transparent (or semi-transparent) material. The proximal end of the outer tube is sealably connected and bonded to the patient port of the proximal terminal. The proximal end of a dark colored, flexible inner tube is sealable connected and bonded to the inspiratory port, and extends through the T-shaped housing, out the patient port, and passes through most of the axial length of the outer tube. The dark color of the inner tube readily permits the user to see through the outer tube to determine whether the inner tube is properly connected.

The inner diameter of the outer tube is sufficiently larger than the outer diameter of the inner tube to permit adequate patient respiration. The distal end of the outer tube is sealably connected and bonded to the exterior of an annular housing which forms a distal terminal. The annular housing of the distal terminal is designed to prevent the distal end of the inner tube from extending beyond the distal end of the outer tube. The entire unit is designed for disposal after a single use.

The UNIVERSAL F™ device offers great advantages over prior dual line and unilimb anesthesia circuits, and respiratory assist devices. However, manufacture of the entire unit requires several complex steps, and must be done with care so that the inner and outer tubes are properly sealed and bonded to the proximal terminal ports at their proximal ends; it is particularly important that the inner tube proximal end be firmly connected to the proximal terminal when the inner tube carries inspiratory gases, since disconnection during use may not allow sufficient oxygen and/or anesthetic gases to reach a patient, which is highly undesirable.

While U.S. Pat. No. 4,265,235, to Fukunaga, teaches that the tubes and terminals of such a unilimb device can be detachable from one another, in practice, the proximal end of the inner tube is firmly bonded to the inspiratory port, since there remains a risk that the proximal end of the inner tube could be disconnected from the inspiratory port during use if a pressure fit (or friction fit) alone is used. Even if detachment of the inner tube is detected, the design of prior art unilimb devices does not facilitate the reconnection of the inner tube to the inspiratory port of the proximal terminal due to the need to pass the inner tube proximal end through the length of the proximal terminal via the patient port so that it can reach and be connected to the inspiratory port. Thus, the unilimb devices currently used generally comprise a proximal terminal having an integrally connected inner tube and outer tube.

Due to its single-use design, the entire unilimb device, including the distal terminal, proximal terminal, inner tube and outer tube, is disposed of after a single use, along with multiple devices usually connected to the patient nozzle, such as a $CO_2$ monitor (capnometer), temperature and humidity controlling and monitoring devices, an $O_2$ controlling and monitoring device, and an infection controlling device (e.g., a filter). Thus, in addition to the inconvenience of requiring fittings (or a housing accommodating same) for these additional devices at the patient nozzle or distal terminal, replacement of these fittings, tubing, and devices after a single use is expensive, and contributes to ever-growing medical wastes, which are sometimes difficult to find disposal sites for. All of the systems described in the aforementioned patens suffer from similar deficiencies. Therefore, there is a need for an improved unilimb device and ventilation system which reduces costs and helps the environment by reducing waste. There is also a need to simplify the construction, and to increase the safety efficacy, and reliability of such devices.

Breathing systems generally provide oxygen to a patient, while removing carbon dioxide produced by the patient. For example, in anesthesia, or intensive care, the patient is provided an artificial breathing atmosphere, in which the physician provides a mixture of gases to the patient. In addition to providing oxygen and a variety of vaporized anesthetic agents to the patient, the physician may permit the patient to rebreathe some expired gases. Rebreathing simply consists of inhaling gases which have been expired, including carbon dioxide. However, assisted respiration/ventilation to a patient must be safe, and hypoxia (i.e., patient oxygen deficiency) must be avoided. Therefore, inspiratory gases are generally provided at high enough pressure, tidal volume and respiratory rate (hyperventilation) to ensure that hypoxia and atelectasis (lunch alveolar collapse) is avoided. Thus, patients are given very high levels of oxygen to avoid hypoxia, but unfortunately they often experience abnormally low carbon dioxide levels (i.e., hypocapnia or hypocapnia), and insufficient carbon dioxide can have a negative impact on vital organs (e.g., brain, heart, splanchnic organs, etc.). However, many physicians believe that increasing arterial carbon dioxide partial pressure ($P_aCO_2$, also referred to as arterial carbon dioxide tension, often reported as mmHg) in patients by increasing the carbon dioxide breathed by the patient (e.g., by increasing the amount of rebreathing) would cause hypoxia. Thus, it was believed that hypercapnia during assisted ventilation was harmful, since it was believed it would be associated with hypoxia. Further, hypocapnia, while it can be harmful, was believed to be less harmful than hypoxia. Therefore, there remains a need for an improved artificial ventilation method which controls or avoids hypocapnia without compromising vital organ tissue perfusion or oxygenation (i.e., avoids hypoxia).

SUMMARY OF THE INVENTION

The present invention provides in one aspect an improved assisted or artificial ventilation system utilizing a unilimb device for providing and exhausting gases from a mammal, and, in another aspect, an artificial ventilation method which avoids hypocapnia and hypoxia. Further aspects of the present invention include new and improved devices for use in the ventilation methods and systems of the present invention.

Aspects of the present invention relate to the surprising discovery by the inventor that concerns about disconnection of the inner respiratory tube, when connected to the inspiratory port of a proximal terminal in breathing circuits utilizing a unilimb device, such as the UNIVERSAL F™ or the "Bain" (U.S. Pat. No. 3,856,051 circuit, can be eliminated by the new proximal terminal construction of the present invention, which facilitates the use of tubing which is intentionally made to be readily attachable and detachable to the proximal terminal ports, rather than sealable connected as in present systems, and yet provide improved function, safety, and serviceability. These breathing circuit manufacturing process is greatly simplified by eliminating the steps of sealably bonding the proximal ends of the inner and outer flexible respiratory tubes to the inspiratory and patient ports, respectively, of the unilimb proximal terminal. The new unilimb proximal terminal of the present invention facilitates the attachment and detachment of respiratory tubing to the proximal terminal, thus resulting in a cheaper and safer breathing circuit. The new unilimb proximal terminal also permits more efficient placement and utilization of the other breathing circuit components in a multifunctional interface incorporating the unilimb proximal terminal. In another aspect of the present invention, an improved coaxial tube device is provided, which is readily attachable and detachable from the new proximal terminal. The improved coaxial tube device has an inner tube in fixed spaced coaxial parallel relationship to an outer tube at its proximal end, such that a single step is required to connect both tubes to the proximal terminal. Thus is made possibly by a fitting within or at the proximal ends of the coaxial inner and outer tubes, which still permits the distal end of the inner tube to axially move with respect to the distal end of the outer tube. As used herein, coaxial refers to the fact that one tube is contained within the other, but the central axis of both tubes need not be aligned.

Aspects of the present invention involve the surprising discovery by the inventor that hypoxia can be avoided while simultaneously creating intentional dead space in the breathing circuit, thereby increasing rebreathing of expired carbon dioxide, which enables maintenance of normal levels of arterial blood carbon dioxide (i.e., normocapnia) during artificial ventilation. Even more surprising is the discovery by the inventor that moderate hypercapnia will not cause hypoxia, provided sufficient oxygen reaches the patient; in fact, moderate hypercapnia can beneficial to a patient (e.g., improve cardiovascular oxygen availability and tissue oxygenation). In yet another aspect of the present invention, the arterial blood carbon dioxide tension ($P_aCO_2$) can be predictably controlled via a predetermined dead space created in the unilimb device breathing tubes (i.e., the volume in the outer tube defined by the space between outer tube distal end and inner tube distal end). The dead space volume may be made adjustable by use of axially extendable and compressible corrugated tubing (which does not rebound to its prior length and maintains its approximate internal diameter despite bending and/or axial length changes); the tubing connects at its proximal end to the patient port of the proximal terminal, and may have dead space calibration markings thereon to permit determination and adjustment of dead space volume contained therein.

In another aspect, the present invention includes an artificial ventilation method which avoids hypocapnia and hypoxia. The method comprises provision of artificial ventilation to a mammal (in which the mammal inspires and expires spontaneously or with mechanical assistance) sufficient to prevent hypoxia, while permitting a sufficient portion of the mammal's expiratory gases to be rebreathed to allow the arterial carbon dioxide tension of the mammal to be between about 35 mmHg to about 45 mmHg (i.e., normocapnia for a human). In another aspect, the mammal's expiratory gases are rebreathed sufficiently to permit the arterial carbon dioxide tension to be between about 45 mmHg to about 95 mmHg (i.e., moderate hypercapnia).

Another aspect of the present invention includes an improved unilimb device useful in providing the above artificial ventilation method. In a preferred embodiment, a unilimb device for use in a breathing circuit includes an outer tube, and an inner tube, each having a proximal end and a distal end. The outer diameter of the inner tube is smaller than the inner diameter of the outer tube, wherein the outer tube can be operably connected at its distal end to a fitting (e.g., endotracheal tube or mask) that can provide artificial ventilation to a mammal. The inner tube is at least partially disposed within the outer tube, and the distal end of the inner tube is disposed within and in direct fluid communication with the outer tube. The proximal end of one of the tubes is connected to an inspiratory gas input (preferably the inner tube), and the proximal end of the other tube is connected to an exhaust outlet. The distal end of the inner tube is axially disposed at a predetermined distance from the distal end of the outer tube to create a dead space in the outer tube between the tube distal ends. The dead space permits the mixing of inspiratory (fresh) gases with expiratory gases from a patient operably connected to the device, and thereby the amount of gases rebreathed by a patient can be related to the dead space volume. This dead space can be predetermined and adjusted to provide for normocapnia or moderate hypercapnia while avoiding hypoxia. In a preferred embodiment, an inner tube and outer tube are provided, which, when operably connected to a mammal to provide respiration, the dead space external of the patient is at least 10 cubic centimeters, and in another preferred embodiment at least 30 cubic centimeters. This dead space may be as small as 10 cubic centimeters for normocarbia in a small mammal (e.g., a human infant), and may exceed 150 cubic centimeters in larger mammals (e.g., adult humans).

In another embodiment, the inner tube is of a fixed length and preferably of a dark color (or has a dark colored band about its distal end); the outer tube can have its length adjusted, and is made of a clear (transparent or semi-transparent) material. The dead space may be adjusted by axial extension or contraction of the outer tube to alter the axial distance between the distal end of the outer tube and the distal end of the inner tube. The outer tube can be formed of section of corrugated tubing, such as for example FLEXITUBE®, which upon axial extension from its compressed axial conformation, or visa versa, will retain its axial length (e.g., will not rebound; i.e., accordion-like pleated tubing). Further, the FLEXITUBE®, when bent, will retain the angle of curvature it is bent to without substantial reduction in the tube's inner diameter. (Suitable corrugated tubing for use in the present invention is used in the Ultra-Flex circuit from King Systems Corporation, of Noblesville, Ind., U.S.A.). The inner tube can be seen through the outer tube and, in one embodiment, the dead space volume can be determined by reference to calibration markings, which are on the outer tube, aligned with the distal end of the inner tube. By placement of a biological contamination filter between the distal ends of the inner and outer tubes and the patient port of the proximal terminal of the unilimb, the current invention makes it possible to safely extend the service life of the proximal terminal beyond a single use. An example of suitable prior art biological contamination filter means, which can be used in some embodiments of the present invention, is the VIROBAC II Mini-Filter by King Systems. Likewise, other adapters and a variety of single use devices, previously connected at the distal or patient fittings, can be reused by connection to the interface at the proximal side of the biological contamination filter. Since the proximal terminal is more complicated to manufacture, this invention permits substantial cost savings by permitting reuse of the proximal terminal and other devices connected thereto, while simultaneously reducing environmental (medical) wastes.

In yet another aspect, the present invention includes a system for use in mammals to provide respiratory and other gases. The system comprises a first breathing conduit having a proximal end and a distal end for providing and exhausting respiratory gases from a mammal, and an interface comprising a breathing circuit operably connected to the proximal end of the first breathing conduit. A biological contamination filer blocks biological contaminants in the first breathing conduit from communicating with the interface components while allowing for adequate transmission of inspiratory and expiratory flows.

The biological contamination filter can be located within the proximal end of the first breathing conduit, or serve as a separate detachable component. In one embodiment of the present invention, a coaxial filter-within-a-filter is provided. The filter apparatus comprises an inner housing having openings at its opposite ends; at least one of the openings has an internal diameter which equals the internal diameter of the inner tube of the breathing conduit, so that the filter device may be attached in a coaxial fashion with the inner tube of the breathing conduit. The inner diameter of the filter device inner housing expand to form a chamber which accommodates a filter having a predetermined diameter to permit sufficient flow therethrough (i.e., flow resistance is inversely proportional to filter surface area). The inner housing is contained within, and in spaced parallel relationship with, an outer housing which is similar or identical in shape, but of sufficiently greater internal diameter throughout to permit fluid to flow between the outer walls of the inner housing and the inner walls of the outer housing. A single disc shaped filter may be contained within the inner housing and radially extend from within the inner housing chamber to the outer housing chamber, or a filter in the shape of an annular ring may be disposed about the outer diameter of the inner housing filter chamber and extend to the inner wall of the outer housing chamber. The inner and outer filter housings may each be constructed from two funnel shaped components, a pre-filtration housing and postfiltration housing (which are mirror images of each other); the two components can be assembled together after placing a filter therebetween at the center of the filter chambers to be formed thereby.

The interface of a preferred embodiment comprises a T-shaped housing, having an inspiratory gas input (inspiratory port), an expiratory gas outlet (expiratory port), and a first respiratory (patient) port. The first respiratory part can be placed in fluid communication, through the biological contamination filter, with a first breathing (respiratory) conduit leading to a patient. The inspiratory port of the proximal terminal connects to and is integral with an internal conduit, which passes through the housing of the proximal terminal, so that the distal end of the internal conduit forms a second respiratory port, which terminates within the first respiratory port. The second respiratory port has a smaller diameter than the first respiratory port, so that gases may flow though the first respiratory port through the space between the exterior wall of the inner conduit and the interior wall of the proximal terminal housing. The new proximal terminal of the present invention permits the ready connection and disconnection of an inner tube of a coaxial respiratory conduit to the inspiratory gas source, since direct sealed fluid communication with the inspiratory port is greatly facilitated by the inner conduit of the new proximal terminal housing. Thus, the prior art difficulties with connection of the inner tube of unilimb devices to the inspiratory port are eliminated, making it possible to avoid sealably bonding the inner flexible respiratory tube to the inspiratory port of the proximal terminal during manufacture.

It is noted that in preferred embodiments of unilimb ventilation devices, the inner tube carries inspiratory gases from an inspiratory gas source, and the outer tube carries expiratory gases. Generally, it is desired that inspiratory gas flow be laminar, while the expiratory gas flow should be turbulent. Turbulent expiratory gas flow is facilitated by the annular shape of the passage between the inner wall of the outer tube and outer wall of the inner tube, as well as by the confluence of gases exiting from the inner tube distal end into the dead space with expiratory air. Further, filtration of the expiratory gases increases turbulent flow in the outer tube, causing a positive and expiratory pressure (PEEP) effect, which helps to maintain positive pressure in the patient airway (to prevent atelectasis). Thus, the filter-within-a-filter device of one embodiment of the present invention helps create turbulent flow in the expiratory gases, when the outer tube is used as the expiratory gas conduit.

In one embodiment, the first breathing or respiratory conduit includes one tube, referred to herein for simplicity as the outer tube, and has a first (proximal) end and a second (distal) end. The outer tube is connected at tis first end through a filter device to the first respiratory port, and has its second, or distal, end directed toward the patient. Both the first and second respiratory ports terminate in and are in fluid communication with the proximal end of the outer tube through one or more biological filters. Thus the first breathing conduit between the patient and the proximal terminal can comprise a single tube, the entire length of which provides a dead space, or mixing chamber for inspiratory and expiratory gases. The first breathing conduit is detachable from the proximal terminal for disposal or sterilization. Use of this system reduces costs and waste, since only the breathing conduit is designed for single use. Another advantage is that the proximal terminal of prior art unilimb devices, such as the UNIVERSAL F™, is no longer disposed of after a single use, and may be a permanent part of the interface.

In one embodiment of the present invention, the respiratory conduit may comprise an outer flexible tube, the length of which can be preselected from various lengths to vary the dead space to a preselected volume. In another embodiment, the outer tube can be axially expandable and compressible (i.e., have accordion-like pleats) to make the dead space adjustable; the dead space can be determined by reference to calibration markings on the outer tube. The calibration markings on the pleated tube may be concealed in the folded pleats, and revealed in opened pleats. The calibration markings may be color-coded bands.

In another aspect of the present invention, the first breathing conduit further comprises an inner flexible tube axially disposed within the flexible outer tube. The inner tube proximal end is connected through a biological contamination filter to the second respiratory port, and the distal end of the inner tube terminates inside of the outer tube. The dead space can be adjusted by adjusting the axial distance between the outer tube distal end and inner tube distal end. In one embodiment, the proximal end of the flexible inner tube and the proximal end of the flexible outer tube are held in spaced parallel coaxial relationship by a rigid fitting, formed of coaxial rigid annuli, a smaller annulus within a larger annulus, which are held in fixed spaced relationship by rigid radial struts extending from the exterior of the inner annulus to the interior of the exterior annulus; in one embodiment, the struts do not extend to the ends of the inner annulus to permit a flexible conduit to be connected thereover. In a preferred embodiment, the fitting connects to the distal end of a filter device, which as a threaded or flanged connector at its proximal end to permit secure attachment to, and simple detachment from, the first and second respiratory ports. In a preferred embodiment, the internal conduit of the interface proximal terminal carries inspiratory gases to the second respiratory port, and the outer tube of the interface carries expiratory gases entering from the first respiratory port. The inner and outer tubes may be of predetermined lengths to provide a predetermined dead space, or the outer tube may be of variable length to permit adjustment of the dead space; calibration markings on a clear outer tube may be aligned with the end of the inner tube to determine dead space volume.

The provision of readily accessible first and second respiratory ports in the distal end of the proximal terminal permits biological isolation of the first breathing conduit, whether it comprises only an outer tube connected to the first respiratory port, or a coaxial outer tube and inner tube which are connected to the first and second respiratory ports, respectively. Thus, only the filter and first breathing conduit need be disposed of (or resterilized) after a single use. The new interface of the present invention permits numerous monitoring and control devices to be included in the interface at the proximal end of the biological filter(s). Various devices contained in detachable modules can be repeatedly utilized with the interface, including devices which were formerly attached to the patient nozzle and disposed of after a single-use. Thus, the new assisted ventilation system of the present invention provides for greatly simplified construction of disposable unilimb single use components, which reduces costs of production and at the same time reduces the quantity of materials requiring replacement after a single use. Further, fewer devices need be crowded about the patient, providing improved surgical safety (less clutter at the patient makes for easier surgical access and safety). Insertion of monitoring and control devices at the proximal, post filtration, end of the breathing system, permits improved control and monitoring of the patients' respiration with a simpler device.

Therefore, the present invention provides a simpler artificial ventilation system, that is easier and less expensive to construct than prior art systems, is easier, safer and less expensive to use, yet provides improved features. Further, the present invention makes possible safer artificial ventilation by providing means and a method for simultaneously preventing hypoxia and hypocapnia. Further details and advantages of the present invention will be appreciated by reference to the figures and description of exemplary embodiments set forth herein.

DESCRIPTION OF THE DRAWINGS

FIG. 5A is a cross-sectional view of an embodiment of a detachable patient coaxial breathing conduit for us in an assisted ventilation system in accordance with the present invention, such as the system of FIG. 4;

FIG. 5B is a cross-sectional view of an alternative embodiment of the detachable patient coaxial breathing conduit illustrated in FIG. 5A which includes a proximal extension;

FIG. 7 is a graphic illustration of the relationship between dead space volume, $V_D$, and the resulting change in patient arterial carbon dioxide tension, $P_aCO_2$, including a linear regression analysis curve, yielding a correlation coefficient, r, of 0.671, and a predicted value for the change in $P_aCO_2$ equal to the product of 2.621 times the $V_D$, added to 1.766; this graph illustrates that the change in $P_aCO_2$ can be reliably predicted as a function of $V_D$ (when $V_D$ is between 0 and 8 ml per kg of patient weight, or $cc^3/kg$;

FIG. 8 is a graphic illustration of the independence of $P_aO_2$ as $V_D$ was varied between about 0 and 8 ml/kg, including a linear regression analysis curve which shows no significant correlation between the two variables in the range tested;

FIG. 10 is a table for estimating the increase in arterial blood carbon dioxide tension in relation to rebreathing circuit apparatus dead space.

DETAILED DESCRIPTION OF PREFERRED EMBODIMENTS

Figure 1:
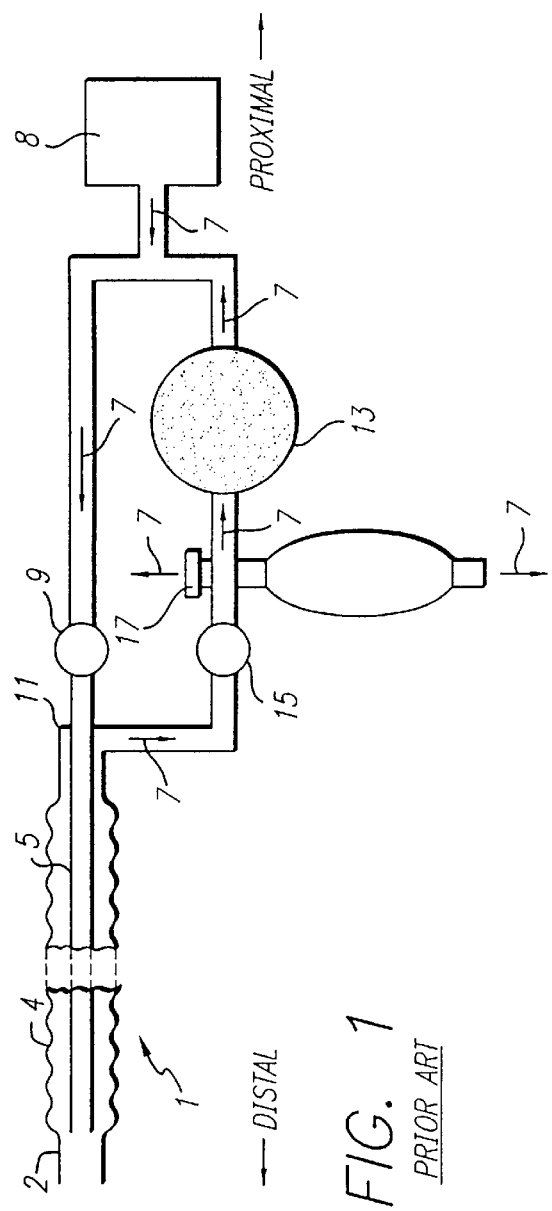
FIG. 1 is a plan and partial cross section view of a prior art assisted ventilation system utilizing a unilimb inspiratory and expiratory gas conduit.

A brief description of a basic prior art artificial ventilation system and unilimb device will facilitate a description of the present invention. With reference to FIG. 1 (FIG. 1), a schematic view of a circle circuit artificial ventilation system utilizing a unilimb respiratory (inspiratory and expiratory gas) conduit is illustrated. A unilimb respiratory (or breathing) conduit 1 may be attached at outlet 2 (otherwise referred to as a nozzle or distal terminal) to a patient endotracheal tube or mask. Breathing conduit 1 is formed out of an outer tube 4 and an inner tube 5. Directional arrows 7 show the preferred direction of gas flow through the system; for example, expiratory air is carried away from a patient through the annular spacing between inner tube 5 and outer tub 4. Inspiratory gases are provided to inner tube 5 from a gas source 8, passing through a unidirectional valve 9. Inner tube 5 penetrates the wall of proximal terminal housing 11; housing 11 essentially comprises a bend in outer tube 4, and the outer wall of tube 5 may be integrally sealed thereto.

A carbon dioxide absorber 13 may be used to remove carbon dioxide from expiratory gases passed therethrough, and the thus-filtered gases combined with inspiratory fresh gases from source 8. Expiratory gases pass from a patient outlet 2 through outer tube 4, then trough unidirectional valve 15 to be recirculated or vented at exhaust port 17.

Figure 2:
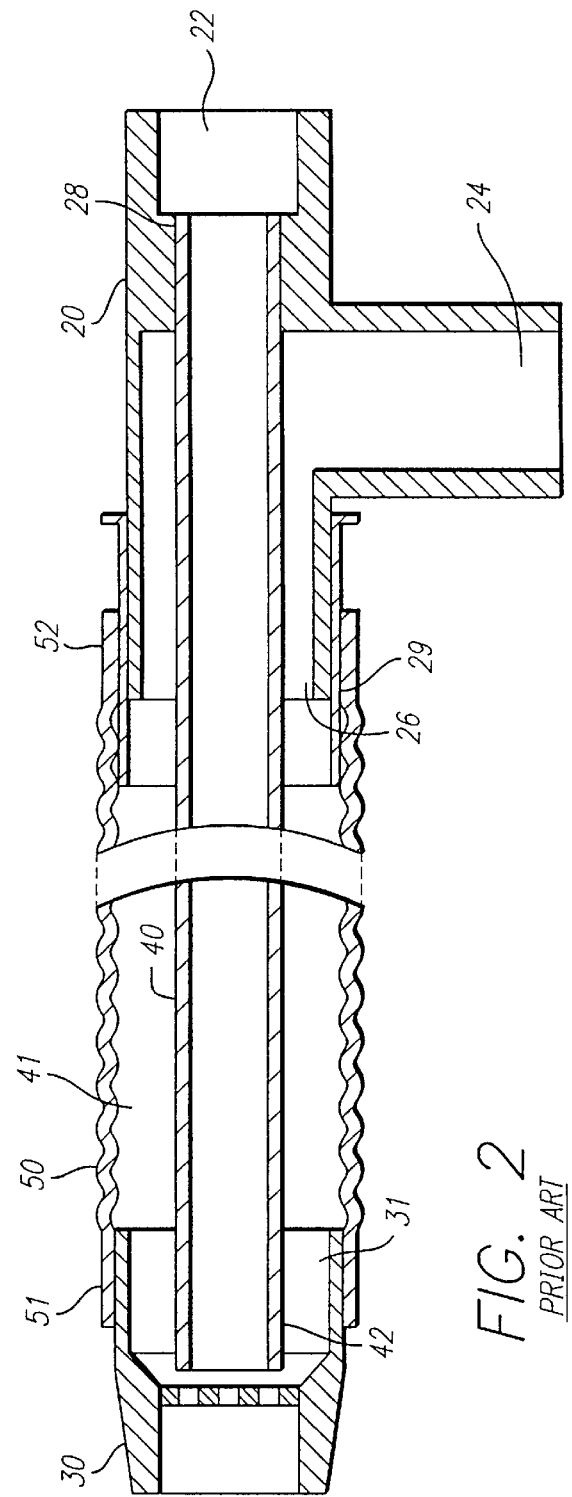
FIG. 2 is a cross-sectional view of a Fukunaga unilimb inspiratory and expiratory gas conduit and proximal terminal as described in detail in U.S. Pat. No. 4,265,235.

With reference to FIG. 2, a Fukunaga unilimb device, such as that described in detail in U.S. Pat. No. 4,265,235 is illustrated. The device comprises a T-shaped proximal terminal 20, a distal terminal 30, a flexible inner tube 40, and a flexible outer tube 50. Since the diameter of inner tube 40 is smaller that the diameter of outer tube 50, an annular space 41 is formed therebetween. The distal end 51 of outer tube 50 is connected to distal terminal 30, which has means 31 for preventing the distal end 42 of inner tube 40 from extending beyond distal terminal 30. Distal end 42 is free of terminal 30 and outer tube 50.

The T-shaped housing of proximal terminal 20 includes an inspiratory port 22, and expiratory port 24, and a patient port 26. Inner tube 40 is connected at its proximal end to inspiratory port 22, and passes through proximal terminal 20 and out of patient port 26. In practice, the remote location of inspiratory port 22 from patient port 26 makes it desirable to sealably bond the proximal end 28 of inner tube 40 to inspiratory port 22, or, optionally, a continuous length of inner tube 40 extends proximally of inspiratory port 22, and distally of patient port 26 to at or near distal end 51 of outer tube 50 (inner tube 40 acting to seal, or being sealably bonded to, inspiratory port 22 at the point of intersection therewith). Likewise, in order to reduce the risk that the inner tube 40 might be dislodged from inspiratory port 22, after being bonded thereto during manufacture, outer tube 50 is bonded at its proximal end 52 to the outer wall 29 of patient port 26, and is bonded at its distal end 51 to distal terminal 30.

A New Proximal Terminal

Figure 3A:
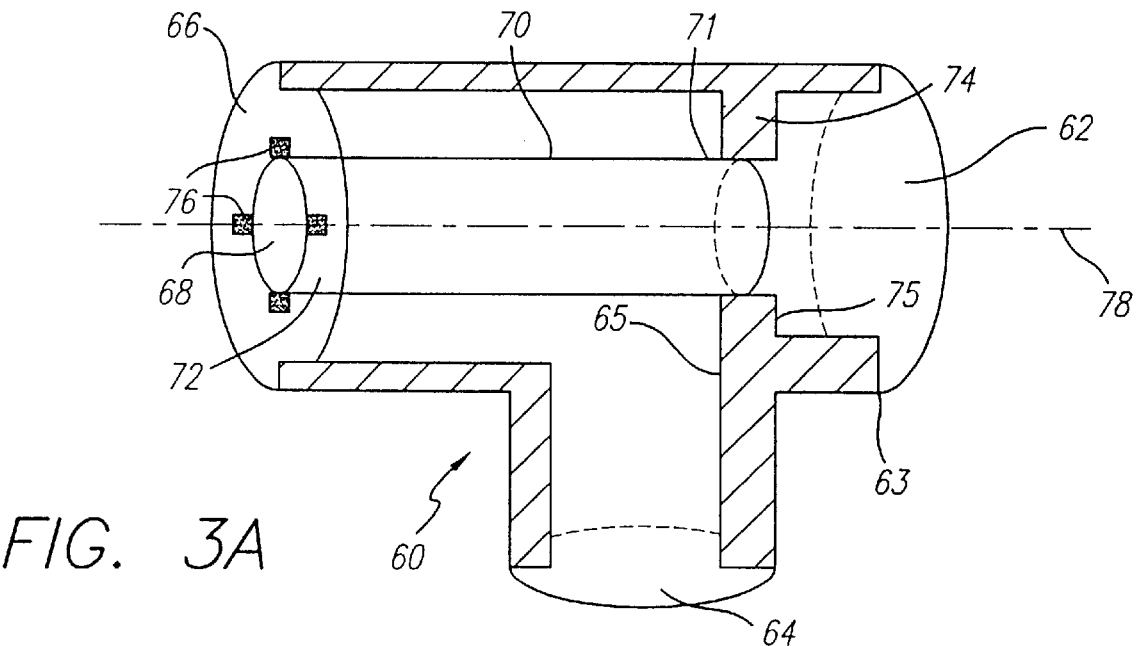
FIG. 3A is a cross-sectional perspective view of the new proximal terminal of the present invention, which includes an inner conduit connected to a second respiratory port.
Figure 3B:
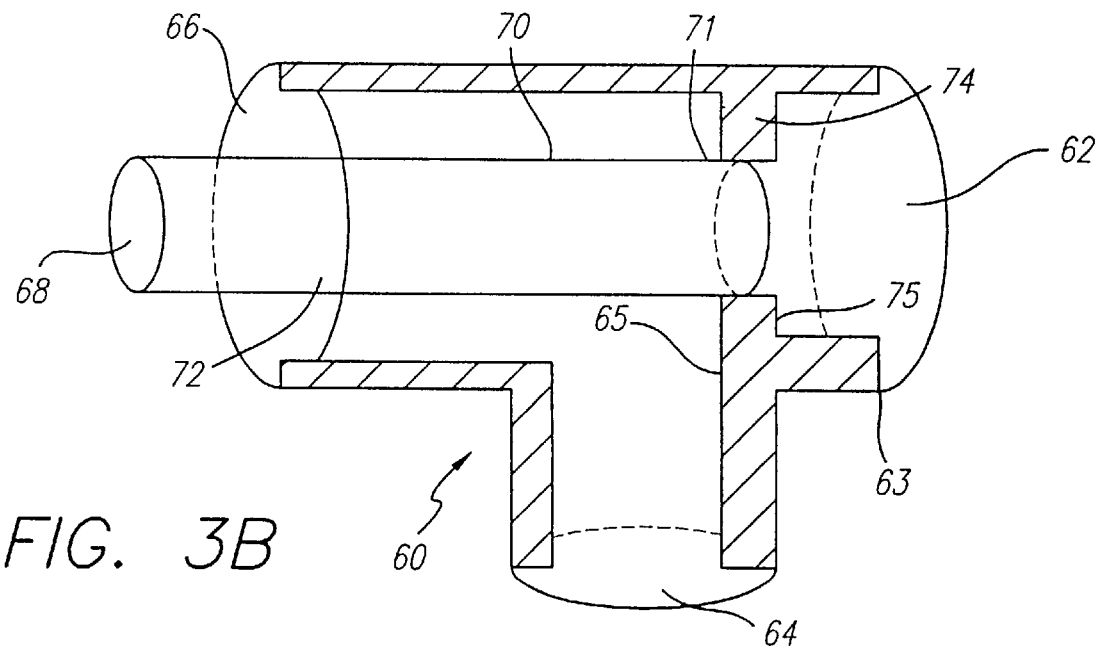
FIG. 3B is a cross-sectional perspective view of an alternative embodiment of the new proximal terminal illustrated in FIG. 3A.

With reference to FIG. 3A, a new and improved proximal terminal 60 is illustrated, which has many surprising advantages over prior art proximal terminals used in unilimb devices. Instead of having three ports, like the proximal terminal 20 of FIG. 2, proximal terminal 60 has four ports, which provide advantages and features not possible with prior art artificial ventilation systems. Proximal terminal 60 comprises a rigid, unitary T-shaped housing, having an inspiratory port 62, an expiratory port 64, a first respiratory port 66, and a second respiratory port 68. Inspiratory port 62 has a step-wise taper from a wider-diameter proximal end 63 to a narrow diameter distal end 65, although the taper may be smooth and continuous, or have other shapes. An inner conduit 70, having a proximal end 71 and a distal end 72 is sealably connected and bonded to inspiratory port 62 at fitting 74. In a preferred embodiment, the outer diameter of inner conduit 70 is sealably bonded to distal end 65 of inspiratory port 62, so as to be integral therewith. An integral annular wall 75 forms the distal end 65 of inspiratory port 62. First respiratory port 66 and second respiratory port 68 form concentric ports about axis line 78, preferably having their concentric openings in the same plane which is perpendicular to axis line 78 of inner conduit 70. Note that second respiratory port 68, while shown axially centered or concentric, within first respiratory port 66, may be off-center with respect to axis line 78 (although this would require that at least a portion of inner conduit 70 to likewise be off-center with respect to axis line 78). In an alternative embodiment shown in FIG. 3B, inner conduit 70 may axially extend outward slightly from first respiratory port 66 so as to further facilitate connection of a tube to second respiratory port 68. Optional flanges 76 may be provided at second respiratory port 68 and/or first respiratory port 66 in order to engage matching threads or flanges of detachable tubular fittings which may be attached thereto. If flexible tubing is to be connected to first and second respiratory ports by pressure fit or friction fit, the walls of the housing 60 should be sufficiently rigid to permit a firm sealed connection. The new proximal terminal may be formed of rigid plastic, such as is typically used in rigid attachments to artificial ventilation systems. Since the new proximal terminal is designed for multi-use, it may also be formed of metal, such as stainless steel. If the terminal is formed of plastic (such as that used in the UNIVERSAL F™ proximal terminal), if may be clear, translucent or opaque. It is important that the walls of the proximal terminal housing near and at the ports have sufficient rigidity to permit connection to conduits, such as the patient respiratory conduit tubes, and conduits connecting to the inspiratory and expiratory ports.

New Unilimb Artificial Ventilation System,
Including New Interface

Figure 4:
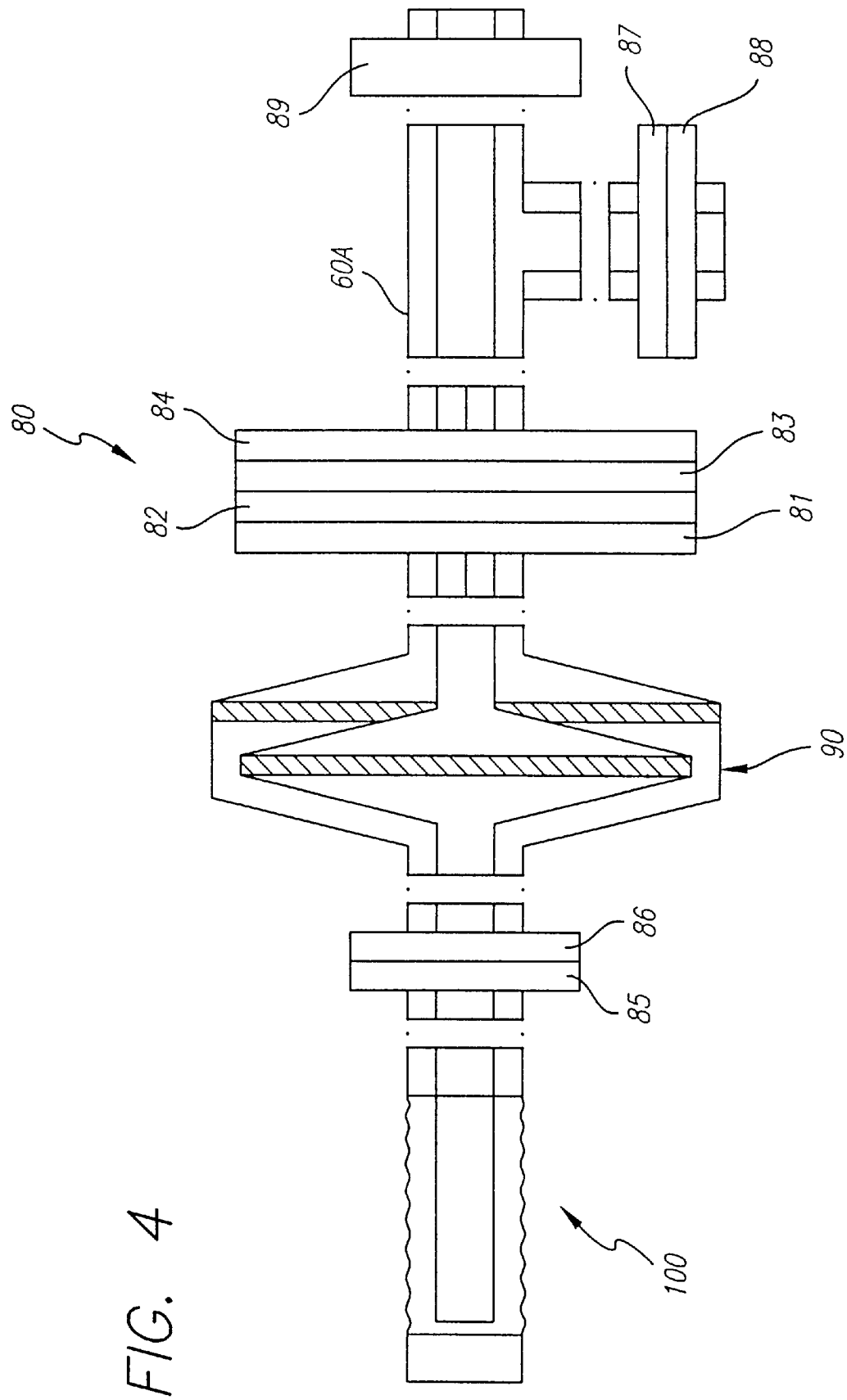
FIG. 4 is an exploded plan view of an assisted ventilation system, with optional components, in accordance with the present invention, including an interface and patient breathing conduits.

With reference to FIG. 4, an exploded plan view of an assisted ventilation system utilizing the new proximal terminal 60 of FIG. 3A is illustrated. In the embodiment of FIG. 4, a block diagram of an interface 80 is shown. Proximal terminal 60 is intended to be manufactured and shipped as a component independent of flexible breathing or respiratory conduit(s) which would lead to a patient, rather than being integrally bound (i.e., bonded) during manufacture to be flexible respiratory conduits as with prior art unilimb devices. Therefore, it need not be disposed of or sterilized after a single use, and it may be incorporated in a single unit, such as interface 80, along with other functional devices 81, 82, 83, and 84, which are illustrated here in block diagram form for simplicity, or it can be placed before or after interface 80. The flexibility of new proximal terminal 60 is illustrated by showing it in block form in 60A. Although four functional devices 81–84 are incorporated in interface 80, more or less than this number may be used. Functional devices may be in the form of readily attachable and detachable modules, so that the ventilation system may be easily modified to meet the requirements of the user. Further, a varying number of optional functional devices, such as devices 85, 86, 87, 88, and 89 may be incorporated in the system, both proximal and distal of proximal terminal 60A.

In the embodiment of FIG. 4, a coaxial breathing conduit 100 (described in more detail below) is connected at its proximal end to functional devices 85 and 86, which in turn are connected to biological filter 90 (another embodiment of which is described in detail below). Inspiratory and expiratory gases must pass through filter 90, thus isolating interface 80, and other system components connected proximally of filter 90, from contamination (infection) by patient expiratory gases conducted by conduit 100.

In one embodiment devices 85 and 86 may comprise an $O_2$ controller (for air dilution) and a $CO_2$ controller (e.g., a rebreathing shunt hole). A reservoir bag (useful during patient transport and/or resuscitation) may be connected at, distal, or proximal or filter 90. Devices 81–84, 87–89 may likewise perform control and/or monitoring functions. For example, devices in modular form can be added so that oxygen can be monitored by an oxygen sensor, and controlled by an air dilution valve, carbon dioxide can be monitored by a capnometer, and controlled by a rebreathing shunt hole; anesthetic gases can be monitored by sensors and controlled by an anesthesia machine; and temperature and humidity can be monitored by appropriate devices, and controlled by an artificial nose.

A New Patient Respiratory Conduit

With reference to FIG. 5A, an alternative embodiment of a patient breathing conduit for use with the proximal terminal of FIG. 3A is illustrated. Breathing conduit 100 consists of a flexible inner tube 110 and a flexible outer tube 120, both connected to proximal fitting 130. Inner tube 110 and outer tube 120 are kept in spaced coaxial relationship at their proximal connection to fitting 130. Fitting 130 has radial flanges 132 which keep rigid inner pipe 134 connected to but spaced from rigid outer pipe 136. Threads or flanges may be optionally provided on inner pipe 134 and/or outer pipe 136 to permit engagement with flanges or threads at second respiratory port 68 and/or first respiratory port 66, or to permit connection to a filter device, which in turn connects to second respiratory port 68 and/or first respiratory port 66.

Distal end 122 of flexible outer tube 120 connects to a rigid annular distal terminal 124. The distal end 112 of flexible inner tube 110 does not axially extend beyond distal terminal 124 or the distal end 122 of outer tube 120. The distal end 112 of flexible inner tube 110 may optionally be connected to distal terminal 124 or to the distal end 122 of outer tube 120, or may be free to move axially within tube 120. The distance between distal end 112 of flexible inner tube 110 and the distal end 122 of flexible outer tube 120 defines a dead space 138. In one embodiment of breathing conduit 100, varying lengths of flexible inner tube 110 and/or flexible outer tube 120 are utilized in order to vary the size of the dead space to a predetermined volume. In another embodiment, outer tube 120 is formed of adjustable-length tubing, so that the dead space can be adjusted by extending or compressing the outer tubing axial length. The outer tubing may be formed of transparent or semi-transparent material, and calibration markings 121 may be included thereon to permit determination of dead space volume by alignment of the distal end 112 of inner tube 110 with the markings 121.

In a preferred embodiment, flexible tubes 110 and 120 are readily attachable to and detachable from fitting 130, and flexible tube 120 is readily attachable to and detachable from distal terminal 124. In one embodiment, flexible tube 110 is not utilized, so that the entire length of tube 120 constitutes dead space. In another embodiment, tube 110 and/or tube 120 connect directly to an interface, which incorporates proximal terminal 60; a biological filter is located between the proximal terminal and tubes 110 and 120.

A New Coaxial Filter

Figure 6A:
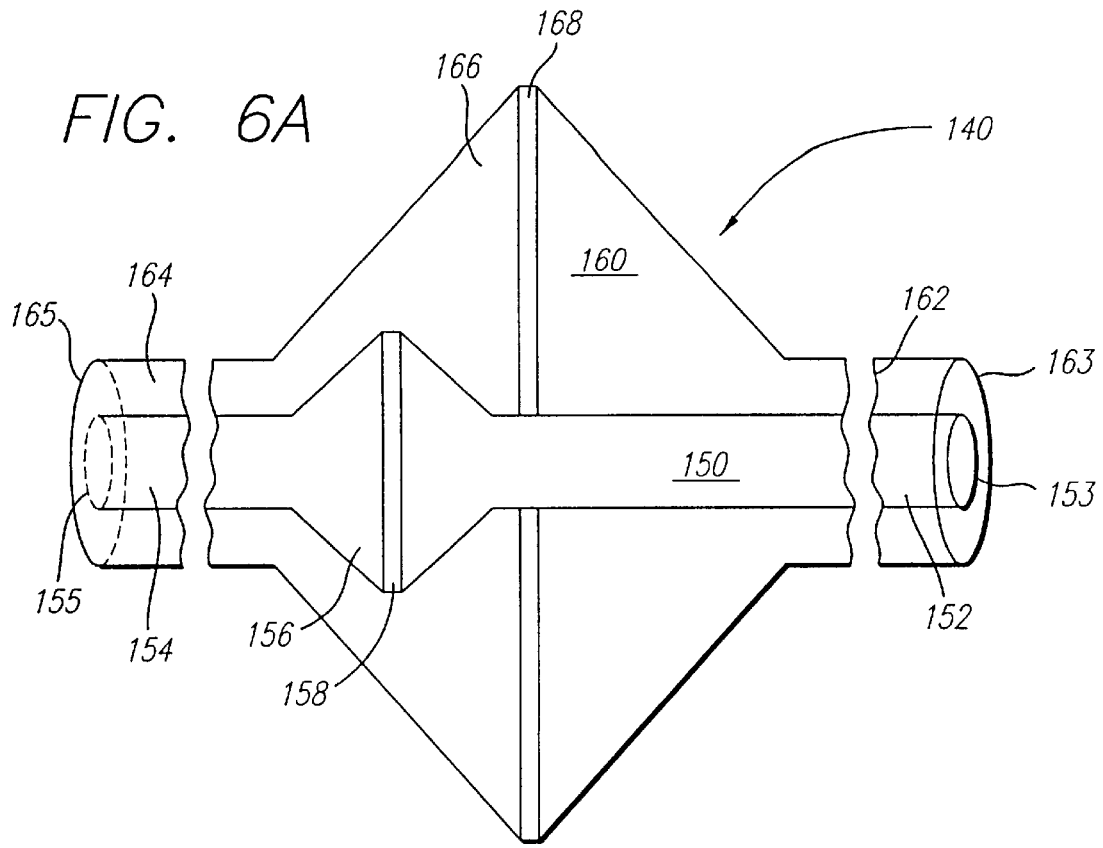
FIG. 6A illustrates a perspective, partial cross-sectional view of an embodiment of a coaxial filter device for use in an assisted ventilation system in accordance with the present invention.

With reference to FIG. 6A, a preferred embodiment of a new coaxial filter device 140 is illustrated, which can be used in a unilimb ventilation device. Filter 140 includes an inner housing 150 and an outer housing 160. Inner housing 150 is formed of tubular conduits 152 and 154 connected to opposed openings in filter chamber 156, which contains a first or inner filter 158. Outer housing 160 is formed of tubular conduits 162 and 164 connected to opposed openings in filter chamber 166, which contains a second or outer filter 168. Flanges or threads may be provided at one or more of the tubular conduit ends 153, 155, 163, and 165, so that the filter may be secured in axial relationship to other tubular fittings. In a preferred embodiment, filter device 140 is connected to a proximal terminal, such as proximal terminal 60 in FIG. 3A, so that inner, tubular conduit 152 is sealably connected to the second respiratory port and outer, tubular conduit 162 is sealable connected to the first respiratory port. In a preferred embodiment, inspiratory gases pass into tubular conduit 152, pass through filter 158, and out of tubular conduit 154 into a breathing conduit, such as breathing conduit 100 illustrated in FIG. 5A, leading to a patient. Expiratory gases pass out of a breathing conduit into the annular spacing between outer, tubular conduit 164 and inner, tubular conduit 154; the expiratory gases then pass through filter 168, into tubular conduit 162, and into the proximal terminal and out of the expiratory port of the proximal terminal, such as port 64 in proximal terminal 60 in FIG. 3A. The preceding gas flow pattern can be reversed if desired.

Figure 6B:
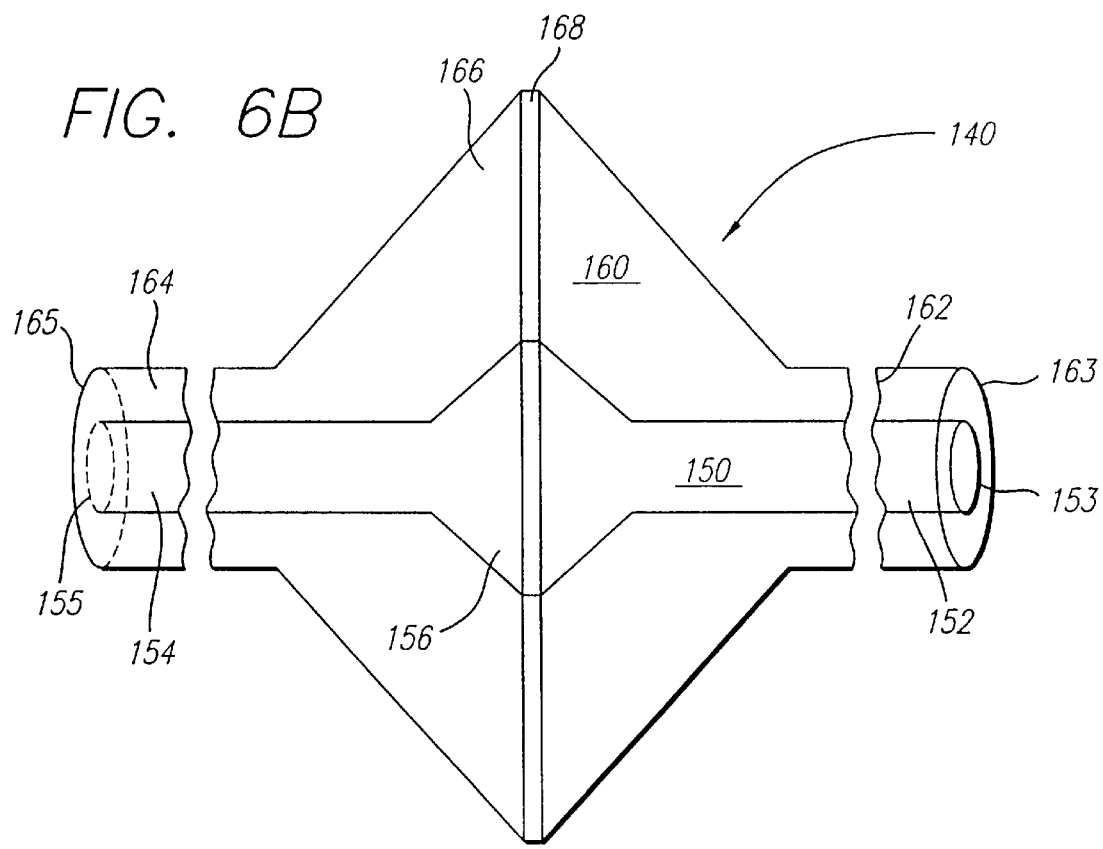
FIG. 6B is a perspective, partial cross-sectional view of an alternate embodiment of the coaxial filter device illustrated in FIG. 6A.

In an alternative embodiment shown in FIG. 6B, filters 158 and 168 can be coplanar, and may even be formed of a single filter disc passing from the inner wall of the outer filter chamber through the wall of the inner filter chamber. In yet another embodiment, inner tubular conduit 152 may axially extend from the end 163 of tubular conduit 162; the extension of tubular conduit 152 is sufficiently long to reach and sealably connect to the inspiratory port of a prior art proximal terminal, which lacks the inner conduit of the new proximal terminal of the present invention. An advantage of the coaxial filter is that one filter device may be used rather than two, using less space in shipping, use, and disposal.

With reference to FIG. 5B, an optional tubular extension 135 is illustrated which may be connected to end 137 of the inner pipe 134. Extension 135, when connected to end 137 is sufficiently long to reach and sealably connect to the inspiratory port of a prior art proximal terminal, which lacks the inner conduit of the new proximal terminal of the present invention.

In a preferred embodiment, the patient, or respiratory, conduit comprises a flexible tube with a diameter between 22 mm and 28 mm, and a length between 100 cm and 1.5 meters. If an inner tube is used with the aforementioned tube, the diameter (or D) is preferably between 11 mm and 15 mm. When using a single tube respiratory conduit, a 22 mm diameter is desirable for adult use, and a 15 mm diameter is desirable for pediatric use. When a coaxial conduit is used, a 28 mm diameter outer tube and 15 mm diameter inner tube are preferred. Dead space volume, $V_D$, in a tube is determined by the relationship:

$$V_D = \Pi (D/2)^2 \times L,$$

where L is the length of the dead space, and D is the outer conduit tube diameter. In a preferred embodiment, the first (outer) and second (inner) respiratory ports of the proximal terminal have inner diameters which are approximately equal to that of the outer tube and inner tube, respectively. Likewise, the inner and outer conduits at the opposed ends of the coaxial filter have inner diameters which are preferably approximately equal to that of the outer tube and inner tube, respectively; and the inner and outer annuli of the proximal fitting have inner diameters which are preferably approximately equal to that of the outer tube and inner tube, respectively.

Thus, the present inventor has described a new unilimb artificial ventilation system, which includes a new patient conduit, a new coaxial filter, and a new proximal terminal, the latter of which may be incorporated into a new multifunctional interface. Various advantages and features of these inventions will be readily apparent to one of skill in the art; by way of non-limiting examples, these new devices are less expensive to manufacture; are easier to use; and have a wider range of uses and configurations than prior art systems; these new devices reduce material wastes, since more components can be reused; yet these devices are safer to use, due to the reduction of equipment required at the patient terminal, and provide for greater monitoring and control.

Artificial Ventilation Which Avoids Hypoxia and Hypocapnia

The unilimb artificial ventilation device of the present invention is ideal for providing artificial ventilation to a patient in which hypoxia is avoided while safely avoiding hypocapnia or even providing moderate hypercapnia. It was surprisingly discovered that normal carbon dioxide levels (normocapnia), or even moderate hypercapnia could be safely induced and/or maintained in a patient without causing hypoxia, as demonstrated by extension data from human subjects, which dramatically illustrates this surprising discovery, and how the unilimb dead space volume can be adjusted to achieve normocapnia or moderate hypercapnia without causing hypoxia.

EXPERIMENTAL

Traditional methods of artificial hyperventilation using large tidal volume ($V_T$>10 ml/kg) and ventilatory frequency (f>10–12 breaths/min) inevitably result in a marked decrease in arterial blood carbon dioxide tension ($PaCO_2$), hypocapnia, and is often associated with serious adverse side effects.

Adverse effects of hypocapnia include: a) Vital organ tissue ischemia/hypoxia, since hypocapnia decreases cerebral, myocardial and splanchnic blood flow, and shifts the oxygen dissociation curve to the left, making the release of oxygen to the tissues difficult; b) Hypocapnia causes reduction of cardiac output and thus decreases the oxygen delivery (i.e. oxygen supply and availability to the tissues); c) Hypocapnia blood and tissue biochemical disturbances: Anaerobic metabolism increases blood lactic acid concentration; and changes in plasma electrolytes (sodium, potassium, calcium, etc.) cause cardiac arrhythmias, metabolic acidosis, tetany, etc.

Therefore, studies were conducted to investigate the effects of ventilation apparatus dead space ($V_D$) on the arterial blood carbon dioxide tension ($PaCO_2$, "Pa" may be used interchangeably with "$P_a$"), and oxygen tension ($PaO_2$) during anesthesia. After institutional approval and patient consent, a total of 301 healthy (ASA class I) adult patients undergoing elective surgery were studied (divided into Study I of 241 patients, and Study II of 60 patients). Anesthesia was induced with a sleeping dose of thiopental; endotracheal (ET) incubation was facilitated with 1 mg/kg succinylcholine. Anesthesia was maintained with 60–70% nitrous oxide in oxygen and 0.5–1.0% halothane, or 0.8–1.5% enflurane, using a conventional anesthesia circle breathing system with $CO_2$ absorption. Intraoperative muscle relaxation was achieved with intermittent pancuronium bromide as required. The patients' lungs were mechanically ventilated using the traditional mode of interbe highly desirable and beneficial to the patients anesthesia and/or to patients undergoing artificial ventilation, for example in the ICU.

TABLE 1

Arterial Blood Gas Data Obtained From 241 Anesthetized Patients (318 samples) During Artificial Ventilation With or Without Apparatus Dead Space (Study I)

| Group | Number of Patients | Body Weight (Kg) | Dead Space Volume ($V_D$ in ml) | | | |
|---|---|---|---|---|---|---|
| | | | 0 | 160–200 | 350 | 550 |
| A | 172 | 60 ± 17 | | | Moderate Hypercapnia | Moderate Hypercapnia |
| B | 61 | 65 ± 9 | Hypocapnia | Normocapnia | | |
| C | 8 | 90 ± 13 | | | | |
| | Group | $FiO_2$ | Control | | | |
| $PaCO_2$ | A | (0.3) | 32 ± 6 | | | |
| mm Hg) | B | (0.3) | 33 ± 4 | 42 ± 9* | | |
| | C | (0.3) | 34 ± 7 | | 46 ± 11* | 51 ± 8* |
| $PaO_2$ | A | (0.3) | 169 ± 40 | | | |
| mm Hg) | B | (0.3) | 163 ± 28 | 164 ± 22 | | |
| | C | (0.3) | 178 ± 125 | | 212 ± 116* | 217 ± 137* |

Mean ± SD, *p < 0.05 vs Control ($V_D$ = 0); Ventilatory setting: $V_\tau$ = 10 ml/kg, f = 10–12 breath/min, I:E ratio = 1:2.

mittent positive pressure ventilation (IPPV) with the following ventilatory settings. Tidal volume ($V_T$=10 ml/kg), ventilatory frequency (f=10–12 breath/min), and inspiratory/expiratory ratio (I:E ratio=1:2) were kept constant throughout the study. $V_T$ was determined with a Wright respirometer placed at the ET tube. Fraction of inspired oxygen concentration ($F_iO_2$=0.3–0.4) was monitored using a galvanic oxygen analyzer (Riken OX-160, Japan). End-tidal $CO_2$ concentration was monitored using an infra-red $CO_2$ analyzer (AIKA, RAS-41, Japan).

After cardio-pulmonary stabilization with the traditional mode of ventilation (i.e. no dead space; i.e., dead space external of the patient of less than 10 ml) was achieved, an arterial blood sample from a radial artery was obtained and immediate analysis of the blood sample was performed using an ABL2 blood gas analyzer (Radiometer, Copenhagen) for control measurement. After control values were taken, one or two of the predetermined dead space volumes, $V_D$, selected from 160, 200, 350, 510 and 550 (ml) was (or were) chosen randomly, and incorporated in the breathing circuit while the same artificial ventilation setting was maintained for 30 min. Thereafter, blood gas measurements were repeated for comparison and statistical analysis was performed. The results of Study I of 241 patients are summarized in Table 1 (divided into Group A, 60 kg±17; Group B, 65 kg±9; and Group C, 90 kg±8), and results of Study II of 60 patients in FIGS. 7–10.

Table 1 shows that the traditional mode of artificial ventilation using IPPV with no apparatus dead space inevitably resulted in a marked decrease in arterial carbon dioxide tension ($PaCO_2$) i.e., hypocapnia. Addition of dead space, $V_D$=160–200 ml, $V_D$=350 ml, and $V_D$=550 ml, significantly increased the $PaCO_2$ to normacapnic and moderate hypercapnic levels respectively, without evidence of substantial $PaO_2$ decreases, i.e. hypoxia, in any of the patients of Groups A, B and C. Study II shows a mathematical regression analysis of the blood gas data obtained from 60 patients (120 samples) during artificial ventilation with varied dead space volumes. Thus, it is demonstrated that a predetermined volume of dead space in the breathing circuit can significantly control the $PaCO_2$ values without evidence of hypoxia during artificial ventilation, as illustrated in FIGS. 7–10 and Table 1. Maintenance of normocapnic levels may FIG. 7 is a graphic illustration of the relationship between dead space volume, $V_D$, measured in milliliters per kilogram of patient body weight (ml/kg, or cubic centimeters per kg of body weight, $cc^3$/kg), and the resulting change in patient arterial carbon dioxide tension, $P_aCO_2$, (measured in mmHg), including a linear regression analysis curve, yielding a correlation coefficient, r, of 0.671, and a predicted value for the change in $P_aCO_2$ equal to the product of 2.621 times the $V_D$, plus 1.766, or in equation form:

$$\Delta PaCO_2(mmHg)=(2.621\times V_D(ml/kg))+1.766.$$

This illustrates that the change (Δ) in $P_aCO_2$ can be reliably predicated as a function of $V_D$ (when $V_D$ is between 0 and 8 ml per kg of patient weight, or $cc^3$/kg).

FIG. 8 is a graphic illustration of the independence of $P_aO_2$ as $V_D$ is varied between about 0 and 8 ml/kg, including a linear regression analysis curve which shows no significant correlation (r is only 0.074) between the two variables in the range tested. Thus, even when dead space volume is large enough to increase $P_aCO_2$ by 15 mmHg (see FIG. 7), there is no significant reduction in $P_aO_2$.

Figure 9:
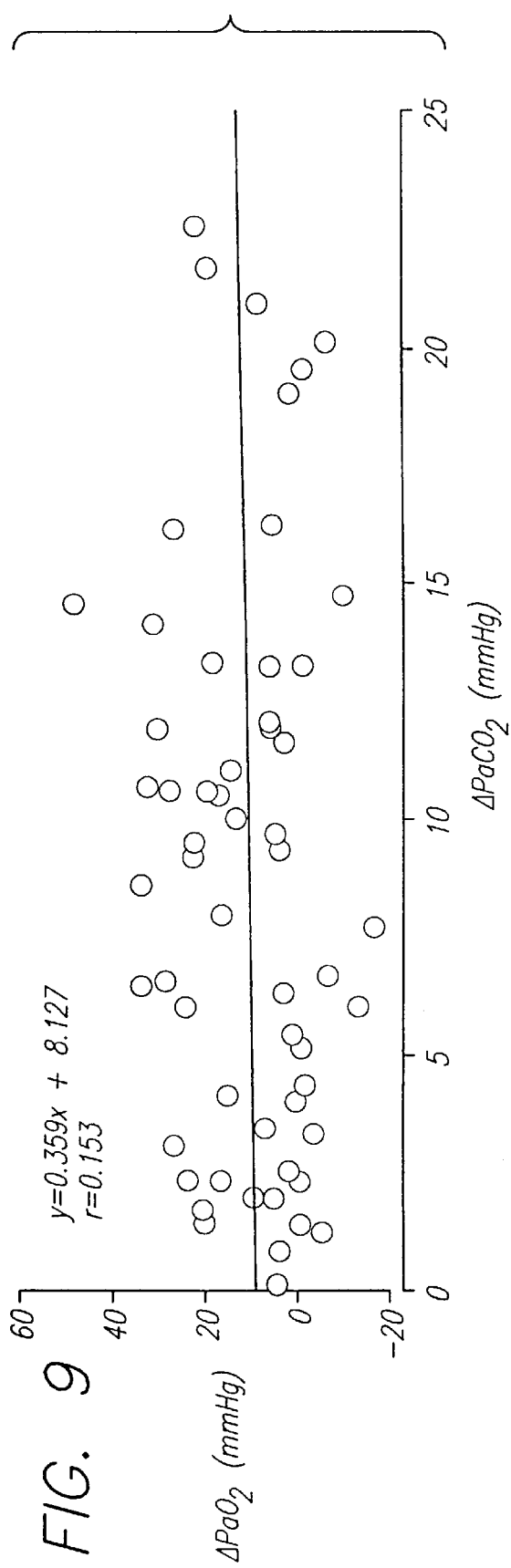
FIG. 9 is a graphic illustration of the independence of changes in $P_aCO_2$ and $P_aO_2$ as $P_aCO_2$ was varied between 0 and 25 mmHg, including a linear regression analysis curve having a correlation coefficient, r, of 0.153, thus showing that increasing $P_aCO_2$ between 0 and 25 mmHg has no significant effect on $P_aO_2$.

FIG. 9 is a graphic illustration of the independence of changes in $P_aCO_2$ and $P_aO_2$ as $P_aCO_2$ was varied between 0 and 25 mmHg, including a linear regression analysis curve having a correlation coefficient, r, of 0.153, thus showing that increasing $P_aCO_2$ between 0 and 25 mmHg has no significant effect on $P_aO_2$.

The table in FIG. 10 is generated by the results of data showed in the graph of FIG. 7 of Study II.

Thus, the artificial ventilation method of the present invention provides for increasing the dead space volume external to a patient to induce and/or maintain normocapnia or moderate hypercapnia while avoiding hypoxia. Without limiting the invention to any particular theory of operation, it is believed that the anatomical dead space present in a patient's respiratory system, including for example that formed by the upper airway (i.e., nose, mouth, laryngeal cavity), trachea and bronchial trees, is at least partially eliminated by endotracheal intubation devices. Thus, the amount of rebreathing from the anatomical dead space is reduced. Further, in order to avoid hypoxia and atelectasis in the prior art, inspiratory oxygen is provided at high pressure, large tidal volume and rapid respiratory rate; this results in hyperventilation and considerable reduction in concentration of arterial carbon dioxide.

Figure 11:
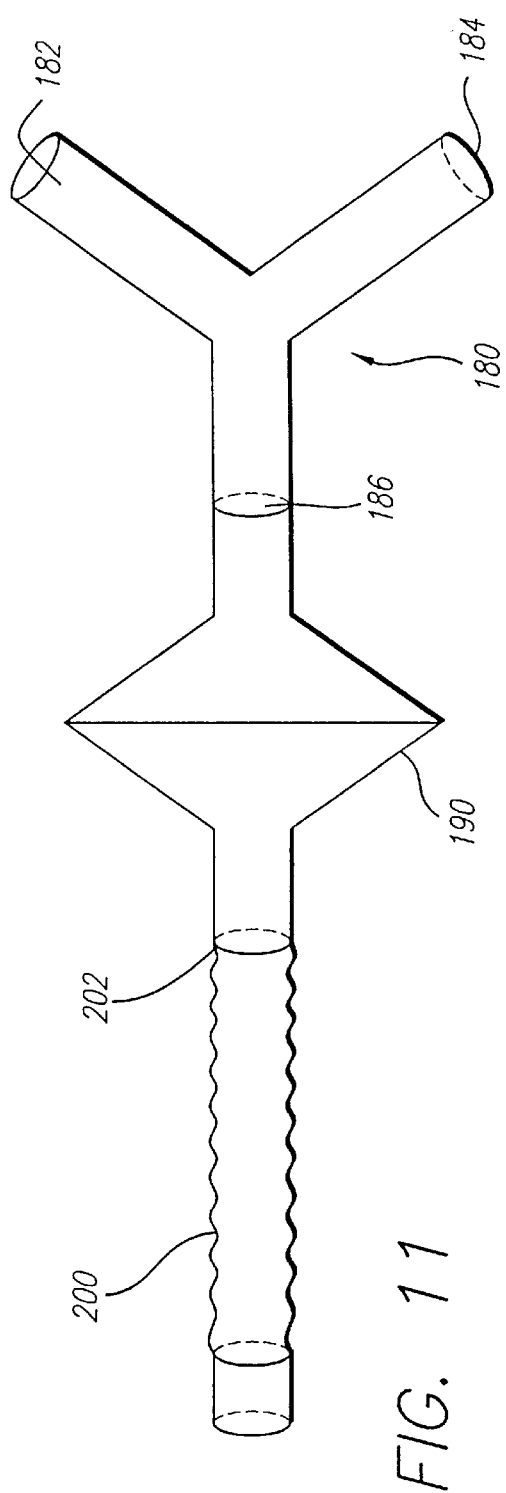
FIG. 11 is a plan view of an assisted ventilation system using a prior art dual hose fitting connected through a filter to a single patient conduit.

In a preferred embodiment, the dead space volume in a unilimb patient respiratory conduit is adjusted to at least 10 ml ($cc^3$), or in an alternative embodiment to at least 30 ml, and may be adjusted to or in excess of 150 ml. The unilimb patient respiratory conduit used may be any of those described herein, or modifications thereto. Although use of the devices described herein is preferred for the foregoing artificial ventilation method, it is anticipated that the discovery that increased carbon dioxide does not necessarily cause hypoxia, so long as sufficient oxygen is provided, may lead to the use of other devices to provide artificial ventilation without hypocapnia or hypoxia. For example, carbon dioxide from an external source may be combined with the inspiratory gases, or a dual limb system may be used, in which additional carbon dioxide is supplied to the patient. For example, with reference to FIG. 11, a Y-shaped fitting 180 is illustrated, which as an input port 182, an exhaust port 184, and a respiratory port 186. Fitting 180 is connected at its distal end to a filter device 190. One way valves, not shown, are proximal of ports 182 and 184 to ensure intermittent positive pressure ventilation. A flexible tube 200 is attached at its proximal end 202 to the distal end of filter device 190. Thus, the entire internal volume of tube 200 serves as dead space. The length and diameter of tube 200 may be selected to achieve a predetermined dead space.

Thus, the assisted ventilation method of the current invention, which avoids hypoxia and hypocapnia, can be provided in some instances with older assisted ventilation systems, while still having the advantages of a single tube for inspiratory and expiratory gases. Tube 200 and filter device 190 may be sealably bonded together, or separate easily attachable and detachable components. Tube 200 can be of varying predetermined lengths of uniform diameter for preselected dead space volume; tube 200 may have axial adjustable length, and have calibration markings at its opposed ends, the distance between the distal and proximal markings thereon precalculated to provide a predetermined dead space (in one embodiment, distal calibration markings can only be seen when the surrounding flexible pleated tubing is axially extended, and are not legible when the surrounding tube pleats are in their folded axially compressed state).

In a preferred embodiment, artificial ventilation is provided to a mammal (e.g.; a human) sufficient to prevent hypoxia, while a sufficient portion of the mammal's expiratory gases are rebreathed to permit the arterial carbon dioxide tension of the mammal to be between about 35 mmHg and about 95 mmHg, and, in another preferred embodiment, the arterial carbon dioxide level of the mammal is kept between about 35 mmHg and about 45 mmHg (i.e., normocapnia).

While preferred embodiments of the invention have been illustrated and described in detail in the figures and foregoing description, the same is to be considered as illustrative and not restrictive in character. For example, while tubes of circular cross-section are used herein, it is anticipated that tubular conduits of varying cross-sectional shape may be used, and that the inner tube of a coaxial tube may or may not be axially centered within the outer tube, or only portions of the inner tube may be axially centered in the outer tube while other portions may be off center. It is also envisioned that the proximal terminal may have more than two conduits passing therethrough, which may connect to a flexible respiratory conduit having more than two lumens.

Thus, it is understood that only the preferred embodiments have been shown and described, and that all changes and modifications that come within the spirit of the invention are desired to be protected.

What is claimed is:

1. A respiratory or ventilator proximal terminal for use in a unilimb artificial respiration device, comprising:
   a unitary housing constructed of a rigid material, said housing comprising a first port, a second port, a third port, a fourth port, an outer tube and an inner tube;
   said outer tube and inner tube each having a first end and a second end, at least a portion of said inner tube being disposed within said outer tube, said second end of said inner tube having a smaller external diameter than the internal diameter of said second end of said outer tube,
   said second end of the said outer tube forming said first port, said second end of said inner tube forming said second port, said first port having an opening which defines a first plane, wherein said second port has an opening which defines a second plane, said first plane and said second plane being substantially coplanar, wherein said second port is surrounded by said first port,
   said first end of said inner tube being sealably bonded into said third port, wherein inspiratory or expiratory gases entering said third port may only pass through said inner tube and exit from said second port, said first end of said outer tube forming said fourth port, said third and fourth ports entering said housing at different locations, wherein inspiratory or expiratory gases entering said fourth port may only pass between the interior of said outer tube and the exterior of said inner tube and may only exit through said first port.

2. The respiratory or ventilator proximal terminal of claim 1, wherein said third port has a distal end and a proximal end, the diameter of said proximal end of said third port being larger than the diameter of said distal end of said third port.

3. The respiratory or ventilator proximal terminal of claim 1, wherein said second end of said inner tube includes a connecting means for firmly connecting said inner tube to a unilimb artificial respiration device.

4. The device of claim 1, wherein said second end of said outer tube includes a connecting means for firmly connecting said outer tube to a unilimb artificial respiration device.

5. A respiratory terminal filter assembly comprising a filter device and a terminal, said filter device comprising
   a filter housing having a proximal end and a distal end, said filter housing containing a first filter chamber and a second filter chamber, said first filter chamber not being in fluid communication with said second filter chamber;
   filter means in said first and second filter chambers;
   a proximal inner conduit and a proximal outer conduit at said proximal end of said filter housing, said proximal outer conduit surrounding said proximal inner conduit to form a proximal expiratory of inspiratory inner fluid path within the interior of said proximal inner conduit and a proximal outer expiratory or inspiratory fluid path in the region between the exterior of said proximal inner conduit and the interior of said proximal outer conduit;
   a distal inner conduit and a distal outer conduit at said distal end of said filter housing, said distal outer conduit surrounding said distal inner conduit to form a distal expiratory or inspiratory inner fluid path within the interior of said distal inner conduit and a distal outer expiratory or inspiratory fluid path in the region between the exterior of said distal inner conduit and the interior of said distal outer conduit;

said first filter chamber being in fluid communication with said proximal inner fluid path and said distal inner fluid path; and said second filter chamber being in fluid communication with said proximal outer fluid path and said distal outer fluid path, said terminal comprising a unitary housing constructed of a rigid material, said unitary housing having a first port, a second port, a third port, a fourth port, an outer tube, and an inner tube, said outer tube and inner tube each having a first end and a second end, at least a portion of said inner tube being disposed within said outer tube, said second end of said inner tube having a smaller external diameter than the internal diameter of said second end of said outer tube, said second end of said outer tube forming said first port, said second end of said inner tube forming said second port, said first end of said inner tube being sealably bonded into said third port, wherein fluid entering said third port may only pass through said inner tube and exit from said second port, said first end of said outer tube forming said forth port, said third and fourth ports entering said housing a different locations, wherein fluid entering said fourth port may only pass between the interior of said outer tube and the exterior of said inner tube and may only exit through said first port;

wherein said proximal outer conduit is connected to said first port and said proximal inner conduit is connected to said second port.

6. The respiratory terminal filter assembly of claim 5, wherein a source of inspiratory gas is operably connected to said third port of said terminal and said fourth port of said terminal is operably connected to an exhaust outlet, such that said inspiratory gas enters and third port of said unitary housing passes through said filter means of said first filter chamber and exits through said distal inner conduit of said filter device, and fluid entering through said distal outer conduit of said filter device passes through said filter means of said second filter chamber and exits through said fourth port into said exhaust outlet.

7. The respiratory terminal filter assembly of claim 5, wherein the second end of said inner tube of said terminal has a connecting means and wherein said proximal inner conduit of said filter device has a mating connecting means, such that when said terminal is connected to said filter device said connecting means of said inner tube of said terminal securely mates with said mating connecting means of said proximal inner conduit of said filter device.

8. The respiratory terminal filter assembly of claim 5, wherein the second end of said outer tube of said terminal has a connecting means and wherein said proximal outer conduit of said filter device has a mating connecting means, such that when said terminal is connected to said filter device said connecting means of said outer tube of said terminal securely mates with said mating connecting means of said outer conduit of said filter device.

9. A respiratory or ventilator proximal terminal for use in a unilimb artificial respiration device, comprising:

a unitary housing constructed of a rigid material, said housing including a first port, a second port, a third port, a fourth port, an outer tube and an inner tube;

said inner tube being at least partially disposed within said outer tube, said outer tube and inner tube each having a first end and a second end, the external diameter of said second end of said inner tube being smaller than the internal diameter of said second end of said outer tube, said second end of said inner tube being disposed within said second end of said outer tube to form an inner inspiratory or expiratory fluid path within the interior of said second end of said inner tube and an outer inspiratory or expiratory fluid path in the region between the exterior of said inner tube and the interior of said second end of said outer tube;

said second end of said outer tube being connected to said first port, said second end of said inner tube being connected to said second port, said first end of said inner tube being connected to said third port and said first end of said outer tube being connected to said fourth port, said third and fourth ports entering said housing at different locations;

wherein fluid entering said third port passes through said inner tube into said inner inspiratory or expiratory fluid path and may only exit through said second port, and fluid entering said fourth port passes through said outer inspiratory or expiratory fluid path and may only exit through said first port.

10. The respiratory or ventilator proximal terminal of claim 9, wherein said third port has a distal end and a proximal end, the diameter of said proximal end of said third port being larger than the diameter of said distal end of said third port.

11. The respiratory or ventilator proximal terminal of claim 9, wherein said third port has a distal end and a proximal end, said first end of said inner tube being sealably bonded to said distal end of said third port.

12. The respiratory or ventilator proximal terminal of claim 9, wherein at least one of said second end of said inner tube and said second end of said outer tube includes a connector for connecting said proximal terminal to a component of a unilimb artificial respiration device.

13. The respiratory or ventilator proximal terminal of claim 9, wherein said second end of said outer tube forming said first port defines a first plane, and said inner tube passes through said first plane such that said second port is distal of said first port.

14. The respiratory or ventilator proximal terminal of claim 9, wherein said second end of said inner tube forming said second port defines a second plane, and said outer tube passes through said second plane such that said first port is distal of said second port.

15. A respiratory conduit assembly for use in an assisted ventilation system having an inspiratory gas input and an exhaust outlet, said respiratory conduit assembly comprising:

a unilimb respiratory conduit, and a proximal terminal, said unilimb respiratory conduit capable of being connected to and disconnected from said proximal terminal by a user at the site of use, said unilimb respiratory conduit having a distal end and a proximal end, said unilimb respiratory conduit including:

an outer flexible tube, an inner flexible tube, said outer flexible tube and inner flexible tube each having a proximal end and a distal end; the outer diameter of said inner flexible tube being smaller than the inner diameter of said outer flexible tube, said inner flexible tube being at least partially disposed within said outer flexible tube, said distal end of said inner flexible tube being disposed within and in direct fluid communication with said outer flexible tube, and a proximal fitting located at said proximal end of said unilimb respiratory conduit, said proximal fitting comprising an inner pipe and an outer pipe maintained in fixed coaxial spaced relationship by spacing means, said outer pipe and inner pipe each having a proximal end and a distal end, wherein said distal end of said inner pipe is operably connected to said proximal end of said inner flexible tube and said distal end of said outer pipe is operably connected to said proximal end of said outer flexible tube;

said proximal terminal having a unitary housing constructed of a rigid material, said housing including a first port, a second port, a third port, a fourth port, an outer terminal tube and an inner terminal tube;

said inner terminal tube being at least partially disposed within said outer terminal tube, said outer and inner terminal tubes each having a first end and a second end, the external diameter of said second end of said inner terminal tube being smaller than the internal diameter of said second end of said outer terminal tube, said second end of said inner terminal tube being disposed within said second end of said outer terminal tube to form an inner terminal fluid path within the interior of said second end of said inner terminal tube and an outer fluid path in the region between the exterior of said inner terminal tube and the interior of said second end of said outer terminal tube;

said second end of said outer terminal tube being connected to said first port, said second end of said inner terminal tube being connected to said second port, said first end of said inner terminal tube being connected to said third port and said first end of said outer terminal tube being connected to said fourth port, said third and fourth ports entering said housing at different locations;

wherein, said unilimb respiratory conduit can be connected to said proximal terminal by operably connecting said first port of said proximal terminal to said outer pipe of said proximal fitting and operating connecting said second port of said proximal terminal of said inner pipe of said proximal fitting to form a first fluid path through said third port, said inner terminal tube, said second port, said inner pipe and said inner flexible tube and a second fluid path through said fourth port, said outer respiratory fluid path, said first port, the region between the exterior of said inner pipe and the interior of said outer pipe, and the region between the exterior of said inner flexible tube and the interior of said outer flexible tube, one of said third and fourth ports of said proximal terminal capable of being operably connected to the inspiratory gas input of the assisted ventilation system while the other one of said third and fourth ports of said proximal terminal is simultaneously operably connectable to the exhaust outlet of the assisted ventilation system, and said distal end of said unilimb respiratory conduit is capable of being operably connected to an airway device connected to a mammal to provide inspiratory gases to the mammal through one of said first and second fluid paths and exhaust expiratory gases from the mammal through the other of said first and second fluid paths.

16. The respiratory conduit assembly of claim 15, further comprising a tubular extension, wherein said tubular extension is connected to one of the group consisting of said inner pipe and said inner terminal tube.

17. The respiratory conduit assembly of claim 15, wherein said proximal end of said outer pipe has an opening defining a first plane, said proximal end of said inner pipe has an opening defining a second plane, said first port has an opening defining a third plane and said second port has an opening defining a fourth plane; said first, second, third and fourth planes being substantially parallel; the axial distance between said first and second planes being suitably adjusted to accommodate the axial distance between said third and fourth planes so that, when said unilimb respiratory conduit is connected to said proximal terminal, said outer pipe firmly engages said first port and simultaneously said inner pipe firmly engages said second port.

18. The respiratory conduit assembly of claim 15, further comprising a filter device, wherein, when said unilimb respiratory conduit assembly is connected to a mammal and a source of inspiratory gas so that inspiratory gases to and expiratory gases from the mammal pass through said respiratory conduit assembly, the inspiratory gases to and expiratory gases from the mammal pass through said filter device.

19. The respiratory conduit assembly of claim 15, wherein said second end of said inner terminal tube has a connecting means and said proximal end of said inner pipe has a mating connecting means, so that, when said proximal terminal is connected to said unilimb respiratory conduit, said connecting means of said inner terminal tube securely mates with said mating connecting means of said inner pipe.

20. The respiratory conduit assembly of claim 15, wherein said second end of said outer terminal tube has a connecting means and said proximal end of said outer pipe has a mating connecting means, so that, when said proximal terminal is connected to said unilimb respiratory conduit, said connecting means of said outer terminal tube securely mates with said mating connecting means of said outer pipe.

* * * * *